United States Patent [19]

Bates et al.

[11] Patent Number: 4,681,915

[45] Date of Patent: Jul. 21, 1987

[54] IMPACT MODIFIED POLYPHENYLENE ETHER-POLYAMIDE COMPOSITIONS

[75] Inventors: Gary M. Bates, Voorheesville; Gregory R. Chambers; Sai-Pei Ting, both of Delmar, all of N.Y.

[73] Assignee: General Electric Company, Selkirk, N.Y.

[21] Appl. No.: 811,808

[22] Filed: Dec. 20, 1985

[51] Int. Cl.$^4$ ............................................. C08L 71/04
[52] U.S. Cl. ................................... 525/148; 525/152; 525/397; 525/905
[58] Field of Search ................... 525/66, 397, 68, 905, 525/148, 152

[56] References Cited

U.S. PATENT DOCUMENTS 4,315,086  2/1982  Ueno et al. .......................... 525/391
4,446,277  5/1984  Brandstetter et al. ................ 525/68

*Primary Examiner*—Jacob Ziegler
*Attorney, Agent, or Firm*—Michael J. Doyle

[57] ABSTRACT

Thermoplastic compositions comprised of compatible combinations of a polyphenylene ether resin and a polyamide resin and which require improved thermal properties can be impact modified with a modifying agent having a core-shell structure comprised of a crosslinked acrylate core and a crosslinked styrenic shell.

16 Claims, No Drawings

IMPACT MODIFIED POLYPHENYLENE ETHER-POLYAMIDE COMPOSITIONS

FIELD OF THE INVENTION

Compositions comprising a combination of polyphenylene ether resin and polyamide resin can be impact modified with a compound comprised of a crosslinked butylacrylate core/crosslinked styrenic shell which is particularly effective for thermoplastic applications requiring thermal stability.

BACKGROUND OF THE INVENTION

Polyphenylene ether resins have been modified with polyamide resins to provide a wide variety of beneficial properties such as excellent heat resistance, chemical resistance, impact strength, hydrolytic stability and dimensional stability compared to either unmodified resin alone.

The improved properties of polyphenylene ether-polyamide compositions have found great utility in thermoplastic applications which take advantage of such properties. Exterior automotive applications such as body panels and wheel covers all benefit from the improved thermal properties of polyphenylene ether-polyamide compositions (PPE/PA compositions). In an automotive application such as a fender part, a satisfactory thermoplastic must be processed at elevated extrusion and molding temperatures. Such parts also experience high temperature finishing processes such as oven baking for paint and other finishes.

Many important thermoplastic applications for PPE/PA compositions also require that the resin be impact modified to provide adequate performance. Impact modification of plastics by incorporation of rubber-like modifiers offers many advantages and disadvantages. Conventional impact modifiers for PPE/PA compositions are either costly or ineffective compared to the impact modification system of the present invention.

Conventional unsaturated impact modifiers such as SBS rubber (styrene-butadiene-styrene copolymer) have shown deficiencies in PPE/PA compositions requiring thermal stability. A rapid drop in impact strength of PPE/PA compositions after high temperature molding conditions over a prolonged period has been attributed to the use of unsaturated rubber impact modifiers.

It has now been discovered that PPE/PA compositions can be improved by combining the base resin with an impact modifier comprised of crosslinked acrylate core/crosslinked styrenic shell in accordance with the description below. In contrast to conventional PPE/PA compositions, those of the present invention have improved melt stability and heat aging characteristics.

SUMMARY OF THE INVENTION

Thermoplastic compositions of the present invention are comprised of:

a. a base resin which is a compatible combination of a polyphenylene ether resin and a polyamide resin; and b. a property improving amount of an impact modifying agent having a core/shell structure wherein the core is a crosslinked acrylate such as butyl acrylate and the shell, which surrounds and interpenetrates the core, is a crosslinked styrenic shell. The crosslinked styrenic shell will preferably be crosslinked polystyrene since this material is particularly useful in combination with PPE resins. It is expected that the crosslinked styrenic shell will typically be comprised of greater than 85 weight percent styrene although other monomer components (such as acrylonitrile) may be useful in small amounts.

Preferred polyphenylene ether resins and polyamide resins as well as means for providing compatible combinations thereof are described below.

In general it is desirable that the polyamide component comprise a continuous phase in the overall composition and, therefore, typically at least 35 percent by weight of the total PPE-polyamide-modifier composition will be comprised of the polyamide component. The remainder of the composition will be comprised of the PPE and core-shell modifier, in typical weight ratios described below.

The preferred modifying component is itself comprised of 40 to 90 weight percent of a crosslinked acylate such as butyl acrylate, which is surrounded and interpenetrated by 60 to 10 weight percent of a crosslinked polystyrene.

DESCRIPTION OF THE INVENTION

Polyphenylene ethers are a well known class of compounds sometimes referred to as polyphenylene oxides. Examples of suitable polyphenylene ethers and processes for preparation can be found in U.S. Pat. Nos. 3,306,874; 3,306,875; 3,257,357; and 3,257,358. Compositions of the present invention will encompass homopolymers, copolymers and graft copolymers obtained by the oxidative coupling of phenolic compounds. The preferred polyphenylene ethers used as base resins in compositions of the present invention will be comprised of units derived from 2,6-dimethyl phenol. Also contemplated are PPE copolymers comprised of units derived from 2,6-dimethyl phenol and 2,3,6-trimethyl phenol.

A particularly useful polyphenylene ether would be poly(2,6-dimethyl-1,4-phenylene ether) having an intrinsic viscosity (I.V.) greater than, approximately 0.10 dl/g as measured in chloroform at 25° C. The I.V. will typically be between 0.40 and 0.50 dl/g. PPE having high glass transition temperatures will ordinarily improve the stiffness of the resin compositions.

The polyamide resins useful in the practice of the present invention are a generic family of resins known as nylons, characterized by the presence of an amide group (-CONH-). Nylon-6 and nylon-6,6 are the generally preferred polyamides and are available from a variety of commercial sources. Other polyamides, however, such as nylon-4, nylon-12, nylon-6,10, nylon-6,9 or others such as the amorphous nylons may be useful for particular polyphenylene ether-polyamide applications.

The polyamides can be provided by a number of well known processes. Nylon-6, for example, is a polymerization product of caprolactam. Nylon-6,6 is a condensation product of adipic acid and hexamethylenediamine. A nylon-6,6 having an average molecular weight of approximately 10,000 is especially preferred for many useful polyphenylene ether-polyamide thermoplastic applications. Preferred polyamides will typically have a relative viscosity of at least 35, in accordance with ASTM Tes Method D789.

In the preferred embodiments of the present invention, a compatibilizing agent will be employed in the preparation of the composition. When used herein, the expression "compatibilizing agent" refers to those polyfunctional, non-rubbery compounds which interact with either the polyphenylene ether, the polyamide or both. This interaction may be chemical (e.g. grafting) or physical (e.g. effecting the surface characteristics of the dispersed phases). In either instance the resulting polyphenylene ether-polyamide composition appears to exhibit improved compatibility, particularly as evidenced by enhanced impact strength, mold line strength and/or elongation.

Many suitable compatibilizing agents are well known for polyphenylene ether-polyamide compositions. Among these compatibilizing agents may be mentioned: liquid diene polymers, epoxy compounds, quinones, oxidized polyolefin waxes, organosilane compounds, and certain polyfunctional organic acids. Suitable polyphenylene ether-polyamide compositions can be provided in the manner taught by U.S. Pat. No. 4,315,086 which is hereby incorporated by reference. In particular, it has been found that a small amount of a material having in its molecule both an anhydride group and a carbon to carbon double bond (e.g. maleic anhydride) is a suitable compatibilizer of polyphenylene ether-polyamide blends. There are, however, many other effective compatibilizing agents.

Those skilled in the art will be able to provide impact improved compositions comprising various proportions of the polyphenylene ether resin, the polyamide resin and the core-shell impact modifier. In general, however, where chemical reistance is a desirable property of the thermoplastic resin, it will ordinarily be necessary that the polyamide resin form a continuous phase of the resin composition. Therefore, to avoid a phase inversion whereby the polyamide phase is discontinuous, the preferred compositions of the present invention will be comprised of a polyamide resin in an amount equal to or greater than approximately 35 percent by weight of the total composition (i.e. the PPE, PA, and core-shell components taken together). The remaining components will be comprised of the PPE and core-shell impact modifier, and may together account for up to approximately 65 percent by weight of the total composition.

Regarding the PPE and core-shell fractions, the ratio of PPE to core shell modifier may range from approximately 99:1 to 50:50 and will typically range from approximately 75 to 80 parts PPE and 20 to 25 parts core-shell modifier.

As might be expected, lower amounts of the core-shell modifier would achieve little useful effect, whereas excess amounts could detract from the physical properties of the thermoplastic resin composition.

The above-described weight ratios and percentages represent the compositional formulations of the present invention. The order of combining the components to provide final products may be varied as will be described below.

The preferable core-shell interpolymer modifiers are those having a crosslinked acrylate rubber core, such as butyl acrylate. Surrounding this crosslinked core is a shell-like structure of crosslinked styrenic resin, preferably styrene, which surrounds and interpenetrates the crosslinked core. Incorporation of small amounts of other monomers such as acrylonitrile and/or methyl methacrylate with styrene in the shell can also provide useful products if the resulting copolymer shell does not cause significant incompatibility with the polyphenylene ether-polyamide matrix. The integrity of such preferable core-shell structures is maintained by the interpenetrating network of the several crosslinked moieties rather than by grafting the structures together.

The core-shell interpolymer compositions may be formed by the following type of two-step, sequential polymerization process:

1. emulsion polymerizing an acrylate monomer charge (herein designated "acrylate", for purposes of the present invention), of at least one $C_2$–$C_{10}$ alkyl acrylate, $C_8$–$C_{22}$ alkyl(meth)acrylate, or compatible mixtures thereof, in an aqueous polymerization medium in the presence of an effective amount of a suitable di- or polyethyleneically unsaturated crosslinking agent for such type of monomer, with the $C_4$–$C_8$ alkyl acrylates being the preferred acrylate monomers for use in this step;

2. emulsion polymerizing a monomer charge of styrene in an aqueous polymerization medium, also in the presence of an effective amount of a suitable dior polyethyleneically unsaturated crosslinking agent for such monomers, said polymerization being carried out in the presence of the product from Step 1 so that the crosslinked (meth)acrylate and crosslinked styrene components form an interpolymer wherein the respective phases surround and penetrate one another.

Such a two-stage polymerization process is analogous to the three step process for producing an acrylate-styrene-acrylonitrile (ASA) terpolymer, as taught by Yu, et al. in U.S. Pat. No. 3,944,631 (which is hereby incorporated by reference).

This core-shell product, which is used as the interpolymer impact modifier in the PPE-polyamide blends of the present invention generally comprises from about 40% to about 90%, by weight, of at least one of the above-identified crosslinked acrylates, and from about 10% to about 60%, by weight, of the crosslinked styrene component. It contains little graft polymerization between the crosslinked styrenic copolymer components and the crosslinked acrylate polymeric component. In the preferred embodiments, the core will comprise 50 to 80 weight percent crosslinked acrylate, based on the weight of crosslinked core and crosslinked shell taken together. Further details regarding this type of polymer composition can be found in the aforementioned U.S. Pat. No. 3,044,731 to A.J. Yu et al. The core-shell interpolymer provided by the foregoing process can be isolated and dried by conventional means and can be provided in powder or pellet form.

Typical PPE-polyamide polymer compositions of the present invention will be comprised of approximately 1 to 30 parts by weight of the core-shell interpolymer modifier based upon 100 parts of the polyphenylene ether-polyamide base resin. It is particularly preferred that about 10 to 20 parts by weight of the core-shell interpolymer additive will be used per 100 parts of the PPE-polyamide base resin. When less than about 2 parts additive are utilized, insufficient beneficial effect will be achieved for typical applications. When greater than approximately 20 parts of additives are utilized, little additional benefit is achieved while other advantageous properties may be diminished for certain applications.

The foregoing constituent ingredients can be compounded and molded by conventional means. The order of mixing and degree of shear experienced during extrusion can be varied. It would be expected that the physical properties could vary as such processing conditions are varied. Those skilled in the art will be able to achieve optimum processing conditions which may vary for different thermoplastic applications.

Thus in one instance, each of the ingredients could be blended and extruded at once, thereby providing thermoplastic resin having a particular property profile. Alternatively it may be desirable to pre-blend or pre-compound some of the ingredients while the remaining ingredients are charged later in a compounding or extrusion process.

In one embodiment, the polyphenylene ether, with or without a compatibilizing agent, could be pre-compounded with the core-shell interpolymer impact modifier. Thereafter, the polyamide resin could be charged to the extruder downstream, at a point sufficient to provide adequate mixing but with minimum risk of degradation due to excess heat.

Additionally, it is expected that conventional additives such as fillers, pigments and flame retarding compounds can be incorporated in the thermoplastic compositions of the present invention, thereby providing a variety of useful products. Specific embodiments of the present invention are taught in the following examples which are not limiting in any way. All parts are by weight unless otherwise indicated.

SYNTHESIS OF CORE-SHELL ADDITIVES

Preparation A: Crosslinked Core/Crosslinked Styrene Shell

A crosslinked polybutylacrylate core having an interpenetrating, crosslinked polystyrene shell was prepared in a five liter, three-necked flask equipped with a heating/cooling jacket, a Teflon blade agitator, a thermometer and a nitrogen purge. The following solutions were prepared:

| Solution A: | n-butyl acrylate | 751.4 g |
| --- | --- | --- |
|  | 1-3 butyleneglycol diacrylate | 1.27 g |
| Solution B: | Sodium Metabisulfite | 1.75 g |
|  | deionized water | 27.4 g |
| Solution C: | Ammonium Persulfate | 4.84 g |
|  | deionized water | 76.1 g |
| Solution D: | styrene | 250.6 g |
|  | divinyl benzene (55% active solution from Dow Chemical) | 2.65 g |

Into the reaction flask was charged: 3,460 g deionized water, the following emulsifying agents: 2.1 g Sipex UB sodium lauryl sulfate (from Alcolac, Inc.) and 4.2 g Aerosol A-268, a disodium sulfosuccinate (from American Cyannamid), and 14.6 g of Solution B. The flask was stirred with $N_2$ sparge at room temperature for 30 minutes, to reduce th $O_2$ content.

Thereafter, 150.5 g of $N_2$ sparged Solution A was added. The flask contents were heated to 55° C. and then 13.5 g of Solution C was added to initiate polymerization.

After 1.5 hours of reaction, a sample showed 4.1% resin solids indicating approximately 96% conversion. The remainder of solution A as well as 14.6 g Solution B and 40.4 g Solution C were added. After 2.5 hours of additional reaction time at 55° C. a sample showed 17.2% resin solids, indicating greater than 97% conversion.

The reaction mixture was cooled to 35° C. and Solution D was added and mixed for 15 minutes at 35° C. The reaction mixture was then heated to 60° C. and the remainder of Solution C was added. The mixture was reacted for 1.25 hours. The temperature was raised to 75° C. and maintained for 45 minutes. A final sample showed 22.4% resin solids indicating a conversion greater than 98%.

The product latex was coagulated in a solution of 0.25 weight percent $CaCl_2$ in methanol at a rate of 1600 ml methanol per 800 ml latex. The coagulum was filtered, rinsed with fresh methanol, and dried in a vacuum oven at 60° C.

The product had a number average latex particle diameter of 211 nanometers, a swell index in methyl ethyl ketone (MEK) of 8.1 and a percent Gel fraction from MEK extraction of 91.1%.

Preparation B Crosslinked Core/Uncrosslinked Styrene Shell

A crosslinked polybutyl acrylate core with an interpenetrating but uncrosslinked styrene shell was provided in the same manner as for Preparation A, except that the divinyl benzene crosslinker in Solution D was eliminated. A product having a final conversion of approximately 97% was recovered as in Preparation A. The product of preparation B had an average latex particle diameter of 203 nanometers, a swell index in MEK of 14.4 and a % Gel from MEK extraction of 63.4%.

EXAMPLES

Experimental thermoplastic blends were mixed by a Henschel mixer, extruded by a 28mm Werner & Pfleiderer twin screw extruder having a temperature profile (set) of 480, 520, 550, 550, 556° F., and injection molded into ASTM specimens by a 3 ounce Newbury injection molding machine at a melt temperature of 570° F. and a mold temperature of 150° F.

The formulations had the compositions shown in Table 1, parts are by weight.

TABLE 1

|  | A* | 1 | B* |
| --- | --- | --- | --- |
| polyphenylene ether resin[a] | 49 | 49 | 49 |
| nylon 6/6[b] | 41 | 41 | 41 |
| maleic anhydride[f] | 1.0 | 1.0 | 1.0 |
| rubber modifiers: |  |  |  |
| (i) styrene-butadiene-styrene and styrene-butadiene[c] | 10 | — | — |
| (ii) crosslinked butyl acrylate core with crosslinked styrene shell[d] | — | 10 | — |
| (iii) crosslinked butyl acrylate core with uncrosslinked shell[e] | — | — | 10 |

*Comparisons
Notes:
[a] poly(2,6-dimethyl-1,4-phenylene)ether having an intrinsic viscosity of approximately 0.45 dl/g as measured in chloroform at 25° C.
[b] Nylon 6/6: NP-10,000 from Nylon Polymer Co.
[c] 80:20 sty-bd-sty triblock / sty-bd diblock mixture, Kraton KD-1102, Shell Chemical Co.
[d] Preparation A, above
[e] Preparation B, above
[f] Maleic anhydride was incorporated to facilitate compatibility of the polyphenylene ether-polyamide base resin.
Additionally, each blend contained 2 parts $TiO_2$, 0.3 parts Irganox 1076 stabilizer and 0.1 part KI.

The effect of the various impact modifiers in polyphenylene ether-polyamide compositions is depicted by the physical properties indicated in Table 2:

TABLE 2

|  | BLEND | | |
| --- | --- | --- | --- |
| Properties | A* | 1 | B* |
| Heat Distortion Temperature (°F. @ 66 psi) | 372 | 387 | 377 |
| Izod Impact (ft-lb/in, notched) | 6.0 | 6.0 | 1.5 |

TABLE 2-continued

| | BLEND | | |
|---|---|---|---|
| | A* | 1 | B* |
| Dynatup Impact (in-lb, max. load) | 451 | 381 | 27 |
| Tensile Yield Strength (psi) | 7350 | 7600 | 7300 |
| Tensile Elongation (%) | 81 | 97 | 18 |
| Flow Channel (in) | 31 | 32 | 33.5 |

It will be evident from the foregoing that the physical properties of polyphenylene ether-polyamide compositions are improved as comparable upon the addition of the crosslinked acrylate core/crosslinked styrene shell modifier utilized by the present invention. Table 3 demonstrates the improved thermal aging characteristics of a composition of the present invention compared to a PPE/PA composition containing a conventional non-hydrogenated impact modifier. 1 The table shows the retention of Dynatup Impact Strength for PPE/PA blends having different impact modifiers, after thermal aging at 375° F.

TABLE 3

| | Initial Dynatup Impact | Retention of Dynatup After | |
|---|---|---|---|
| | | 2 HRS | 4 HRS. |
| Blend A[a] | 452 in-lb | 73% | 23% |
| Blend 1[b] | 381 | 106% | 96% |

[a]from Table 1 above, contains unsaturated Kraton D-1102 modifier
[b]from Table 1 above, contains crosslinked acrylate core/crosslinked styrene shell modifier.

We claim:

1. A thermoplastic resin composition comprising:
   a. a base resin comprising a compatible combination of a polyphenylene ether resin and a polyamide resin; and
   b. a property improving amount of an impact modifying agent core-shell structure consisting essentially of of a crosslinked acrylate core and an interpenetrating, crosslinked styrenic shell wherein the agent is prepared by polymerization a styrene with polyethylenically unsaturated cross-linking agent in the presence of the crosslinked acrylate core.

2. A composition as in claim 1 wherein said polyphenylene ether resin is a polymer or copolymer comprised of units selected from the groups consisting of 2,6 dimethyl phenylene units and 2,3,6 trimethyl phenylene units.

3. A composition as in claim 2 wherein said polyphenylene ether resin is poly (2,6-dimethyl-1,4-phenylene ether).

4. A composition as in claim 2 wherein said polyphenylene ether resin has an intrinsic viscosity of, approximately 0.30 to 0.60 dl/g as measured in chloroform at 25° C.

5. A composition as in claim 1 wherein said polyamide resin is selected from the group consisting of polyamide-6, polyamide-6,6, polyamide-12, and polyamide-6,9.

6. A composition as in claim 1 wherein the polyamide resin comprises at least 35 percent by weight of the total composition.

7. A composition as in claim 1 wherein the weight ratio of polyphenylene ether resin to said core-shell modifying agent varies from, approximately, 99:1 to 50:50.

8. A composition as in claim 1 wherein said crosslinked acrylate core is a crosslinked alkyl acrylate core.

9. A composition as in claim 8 wherein said alkyl acrylate is butylacrylate.

10. A composition as in claim 1 wherein said modifying agent is comprised of 40 to 90 weight percent crosslinked acrylate core and 60 to 10 weight percent crosslinked styrenic shell, based upon the weight of core and shell together.

11. A composition as in claim 1 wherein said crosslinked styrenic shell is at least 85 weight percent polystyrene, based upon the weight of said shell.

12. A composition as in claim 11 wherein said crosslinked styrenic shell is crosslinked polystyrene.

13. In a method for improving the thermal stability of impact modified polyphenylene ehter-polyamide compositions, wherein the thermoplastic base resin is a compatible combination of a polyphenylene ether resin and a polyamide resin, the improvement base resin with a property improving amount of an impact modifier having a core-shell structure consisting essentially of of a crosslinked acrylate core and an interpenetrating crosslinked styrenic shell wherein the agent is prepared by polymerization a styrene with polyethylenically unsaturated cross-linking agent in the presence of the crosslinked acrylate core.

14. A method as in claim 13 wherein said polyamide resin comprises, at least approximately, 35 parts by weight per 100 parts of the total composition.

15. A method as in claim 13 wherein said impact modifier is comprised of, approximately, 40 to 90 weight percent crosslinked acrylate, and 50 to 10 percent by weight of said crosslinked styrene component.

16. A product made by the method of claim 13.

* * * * *